United States Patent [19]

Link et al.

[11] 4,009,709
[45] Mar. 1, 1977

[54] APPARATUS AND PROCESS FOR DETERMINING SYSTOLIC PRESSURE

[75] Inventors: William Trevor Link; Henry Ferdinand Rugge, both of Berkeley; William David Jansen, Menlo Park, all of Calif.

[73] Assignee: American Optical Corporation, Southbridge, Mass.

[22] Filed: May 15, 1975

[21] Appl. No.: 578,047

[52] U.S. Cl. .................... 128/2.05 A; 128/2.05 M
[51] Int. Cl.² .................................. A61B 5/02
[58] Field of Search ............ 128/2.05 A, 2.05 M, 128/2.05 N, 2.05 G, 2.05 R, 2.05 T

[56] References Cited

UNITED STATES PATENTS

| 3,227,155 | 1/1966 | Erickson et al. | 128/2.05 R |
| 3,903,872 | 9/1975 | Link | 128/2.05 A |

OTHER PUBLICATIONS

Link, W.T., *Norse Systems Inc.* Report (NORIR-74-1), Aug. 1974, 12 pages.
*Med. & Biol. Engng.*, vol. 7, pp. 95-97, 1969.

*Primary Examiner*—Kyle L. Howell
*Attorney, Agent, or Firm*—Stephen A. Schneeberger; William C. Nealon; H. R. Berkenstock, Jr.

[57] ABSTRACT

A conventional pressure cuff is attached to a living test subject. First means are provided for changing pressure in the cuff and thereby applying pressure to the subject. Second means communicating with the cuff are provided for measuring a quantity proportional to a time-dependent fluctuating component representative of pulsatile pressure within a blood vessel of the subject, the second means having a frequency response of at least about five times the subject's pulse rate, whereby the fluctuating quantity is proportional to amplitude of pulsatile pressure. The maximum value of the fluctuating quantity is determined as applied cuff pressure is changed. Third means are provided for determining when the fluctuating quantity is about one-half its maximum value for applied cuff pressure greater than the pressure applied when the maximum value occurred or resulted. Systolic pressure, which is equal to applied cuff pressure when the fluctuating quantity is about equal to one-half the maximum value of the fluctuating quantity, is then read out on suitable instrumentation.

15 Claims, 7 Drawing Figures

APPARATUS AND PROCESS FOR DETERMINING SYSTOLIC PRESSURE

BACKGROUND OF THE INVENTION

1. Field of the Invention

The present invention relates generally to the field of blood pressure monitoring, and more particularly to automatic monitoring of systolic blood pressure.

2. Description of the Prior Art

The prior art is replete with devices for measuring systolic pressure of a living subject. An old and simple device is a pressurizable cuff used in combination with a mercury manometer which reads pressure in the cuff and a stethoscope which is used to listen to Korotkoff sounds. More complicated methods and apparatus based on the same principle of listening to the Korotkoff sounds replace the mercury manometer with a mechanical or electromechanical pressure gauge and utilize microphonic detection of the Korotkoff sounds which are analyzed electrically. In another advanced method of measuring blood pressure, the distance from a blood pressure cuff to the wall of an artery is accurately determined by measuring Doppler shifts of sound waves reflected by the artery. The distance to the artery varies as a function of pressure within the somewhat pliable walls thereof. In yet other methods for measuring blood pressure intrusive devices are often inserted directly into blood vessels.

Oscillometric methods of determining systolic pressure are also well known in the art. In such methods, the operator observes a representation of the strength of pulsations of pressure within an artery. This can be done visually, as by watching the extent of bouncing of the top of a mercury column in a mercury manometer which is in pressure-communication with a cuff, or indirectly as by measuring the occlusion which occurs to a blood vessel in the pinna of the ear as pressure is exerted thereon, as in U.S. Pat. No. 3,227,155. Oscillometric methods of determining systolic pressure generally define systolic pressure to be the maximum applied pressure at which threshold oscillations are observed to occur. With a typical mercury manometer and pressurizable cuff, this pressure would then be the highest pressure at which the operator noted bouncing in the top of the mercury column as the pressure in the cuff was slowly and relatively uniformly reduced. However, there are inaccuracies associated with this method for determining threshold oscillations, since the mercury column does not noticably respond to narrow-width pressure pulses; i.e., the energy associated with a narrow-width pulse is insufficient to noticably move the comparatively high inertia mercury column. In other words, because of relatively slow response time of a mercury manometer (or the apparently selectively slow occlusion rate of the pinna of the ear) the quantity actually being measured is proportional to an integral of the pressure pulse rather than actual amplitude thereof. Oscillometric methods based on observing threshold oscillations are thus inherently somewhat inaccurate, where "threshold" is a parameter or term that generally may be hard to rigorously and exactly define anyway.

Nevertheless, methods based on listening to Korotkoff sounds are relatively accurate for measuring systolic pressure, but are burdened with requiring use of a microphonic detector if they are to be instrumented. The method based on Doppler shifts is also accurate, but also is burdened with requiring special measuring apparatus, and has a further shortcoming in that it is sensitive to positioning of the measuring apparatus relative to the artery.

The present invention provides a solution to the problems associated with inaccurate systolic blood pressure measurement and monitoring provided by simple devices of the prior art. The present invention also provides a solution to the problems associated with complex and special microphonic and other apparatus employed in the more accurate prior art devices for measuring and monitoring systolic blood pressure. The present invention thus provides apparatus and method for automatically measuring and monitoring systolic blood pressure, employing a simple cuff and automatically controlled instrumentation.

A related U.S. patent application Ser. No. 445,559 filed Feb. 25, 1974 and now U.S. Pat. No. 3,903,872, issued Sept. 9, 1975, and assigned to the assignee of the present invention, entitled "Apparatus and Method for Producing Sphygmometric Information," is directed to diastolic blood pressure, and is incorporated herein by reference.

SUMMARY OF THE INVENTION

In one sense, the invention comprises apparatus for determining systolic pressure, comprising: a pressure cuff attachable to a living test subject adjacent a blood vessel; means for changing pressure in the cuff and thereby applying pressure to the subject; means communicating with the cuff for measuring a quantity proportional to a time-dependent fluctuating component representative of the pulsatile pressure within the blood vessel whereby the quantity is proportional to amplitude of the pulsatile pressure; means for determining the maximum value attained by said quantity as the applied pressure is changed; means for storing a representation of the maximum value; means for determining when the quantity is substantially equal to about one-half of the maximum value for an applied pressure greater than the pressure applied when the maximum value occurs or results; and means for reading out the applied pressure corresponding to said quantity being substantially equal to about one-half of the maximum value, said read-out pressure corresponding to the systolic pressure of said subject.

In another sense, the invention comprises a process or method for determining systolic pressure, comprising: applying pressure to a living test subject by changing pressure in a pressure cuff attached to the subject adjacent a blood vessel; measuring at said cuff a quantity proportional to a time-dependent fluctuating component representative of the pulsatile pressure within the blood vessel, said quantity being proportional to amplitude of the pulsatile pressure; determining the maximum value attained by said quantity as the applied pressure is changed; storing a representation of the maximum value; determining when the quantity is substantially equal to about one-half of the maximum value for an applied pressure greater than the pressure applied when the maximum value occurs or results; and reading out the applied pressure corresponding to the quantity being substantially equal to about one-half of the maximum value, the read-out pressure corresponding to the systolic pressure of the subject.

The advantages of employing the present invention in automatic blood pressure monitoring thus include at least: simple cuff hookup to the subject, automatic cuff inflation and pressure measurement, and accurate systolic pressure monitoring.

It is thus a general object of the present invention to provide an improved apparatus and process/method for taking blood pressure measurements.

It is another object of the present invention to provide an improved apparatus and process/method for automatically monitoring systolic blood pressure, in which the need for a double-cuff and/or an arm-mounted transducer is eliminated.

It is yet another object of the present invention to provide an apparatus and process for determining systolic pressure, which apparatus and process are extremely accurate and compatible with pressure-transducer-based measurements of diastolic pressure without requiring extra instrumentation.

Other objects and advantages of the present invention will be apparent to those skilled in the art after referral to the detailed description of the preferred embodiment in conjunction with the appended drawings.

DETAILED DESCRIPTION OF THE PREFERRED EMBODIMENT

Figure 1:
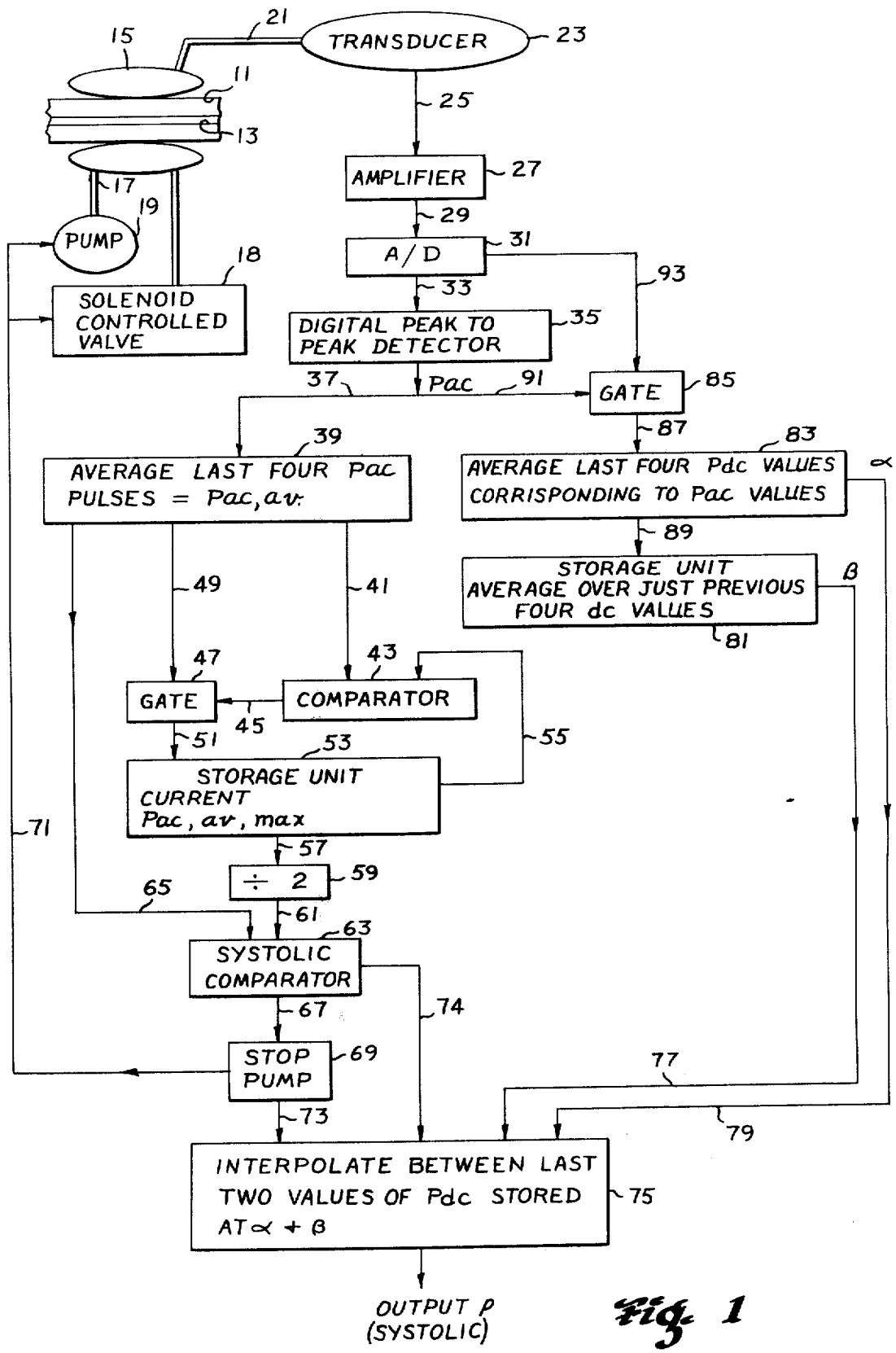
FIG. 1 illustrates in a block diagram the apparatus and process of the present invention.

Referring first to FIG. 1, there is arm 11 of a test subject with artery 13 therein, the arm being surrounded by a typical blood pressure cuff 15. Typically, the brachial artery located in the upper arm is employed for this type of blood pressure measurement. Attached to the cuff via conduit 17 is pump 19. Also attached to the cuff via conduit 21 is pressure transducer 23 having a frequency response of at least about five times the pulse rate of the test subject. The pressure transducer 23, in order to satisfy the criterion of having a frequency response of at least about five times the pulse rate of the subject, will generally have a frequency response of at least about 10 Hertz. The pressure transducer serves to measure pressure within the cuff, which pressure is the sum of pressure supplied by the pump and a fraction of pressure produced by blood pressure fluctuation within the artery. Since the transducer has the required frequency response, the fluctuating portion of output thereof represents amplitude of pulsatile pressure rather than the integral thereof. Output of transducer 23 proceeds as represented by line 25 to amplifier 27, wherein the signal is amplified and passed therefrom, as represented by line 29, to analog-to-digital (A/D) coverter 31. Output converter the analog-to-digital converter is fed, as represented by line 33, to digital peak-to-peak detector 35, in which a quantity proportional to the time-dependent fluctuating component representative of pulsatile pressure within the blood vessel is calculated.

An output comprising said quantity from the digital peak-to-peak detector 35 proceeds, as represented by line 37, to averaging unit 39, wherein an updated average value for the present and three immediately previous quantities proportional to the time-dependent fluctuating component representative of the pulsatile pressure within the artery 13 is determined. This average value is fed, as represented by line 41, to comparator 43. The comparator 43, as represented by line 45, controls gate 47. The gate 47 serves to allow the averaging unit 39, as represented by line 49, to load a selected value of the quantity, as represented by line 51, into storing unit 53. The value of the quantity being stored in storing unit 53 is supplied to the comparator 43, as represented by line 55. Within comparator 43, stored tentative previous representations of the maximum value of said quantity are compared with current values of said quantity introduced into the comparator 43, as represented by line 41. When a value of said quantity supplied to the comparator 43, as represented by line 41, is greater than the quantity tentatively stored in the storage unit 53, as supplied to the comparator 43, as represented by line 55, then gate 47 is activated by the comparator 43, as represented by line 45, and the larger value of said quantity replaces the tentative maximum value in storage unit 53.

The tentative maximum value of said quantity is introduced, as represented by line 57, into a halving unit (divide-by-two) 59 wherein it is divided in half. The divided-in-half value is then introduced, as represented by line 61, to a systolic comparator 63. Also supplied to the systolic comparator 63 is the (now) current average of four most previous measurements of said quantity. This is supplied from the averaging unit 39, as represented by line 65. When systolic comparator 63 determines that the average quantity being supplied thereto, as represented by the line 65, is less than or equal to one-half of the tentative maximum value being supplied thereto, as represented by line 61, the systolic comparator 63 orders, as represented by line 67, the switching means 69 to stop the pump 19 and bleed the cuff 15 through solenoid control valve 18 and conduit 20, the stop-and-bleed order being represented by line 71.

The switching means 69, as represented by line 73, and systolic comparator 63 as represented by line 74, also order interpolating unit 75 to interpolate between values of the applied pressure, that is, the pressure being applied to cuff 15 by pump 19, so as to determine the precise applied pressure corresponding to said quantity being about one-half of said maximum value.

Values of applied pressure are supplied to interpolation unit 75, as represented by lines 77 and 79. Line 77 represents introduction of the applied pressure value for measurement just before the quantity became less than one-half the maximum value, and line 79 represents applied pressure when the quantity was equal to or slightly less than one-half the maximum value. These values of the applied pressure are supplied, as represented by lines 77 and 79, from storage unit 81 and computing and averaging unit 83 respectively. The values of the applied pressure are supplied to averaging unit 83 by gate 85, as represented by line 87. The value of the just-previous applied pressure is supplied to storage unit 81 from averaging unit 83, as represented by line 89. The value of the applied pressure is supplied to gate 85 from digital peak-to-peak detector 35, as represented by line 91. The gate 85 is triggered by the output of the analog-to-digital converter 31, as represented by the line 93. Hence, one value of applied pressure passes into the average unit 83 for each pulse which passes into the averaging unit 39. The applied pressure and pulse pressure values are easily separated from one another because of their very different frequencies, the applied pressure being usually a slow ramp function and the pulse pressure having a frequency of about 1 Hertz. In the preferred embodiment of the invention, pump 19 is adjusted to repetitively apply an increasing ramped pressure to cuff 15.

The apparatus and process of the invention can also, however, be made to operate with a pump which sequentially applies a decreasing pressure including decreasing ramped pressure to the cuff. In this case it is necessary to provide a memory unit wherein successive values of applied pressure and of corresponding amplitude of the pulsatile quantity measured are stored for later comparison with one-half of the eventually determined maximum amplitude. The maximum value of the pulsatile quantity will not be determined until after the cuff pressure corresponding to systolic pressure has been passed as the pressure drops. In other words, the half amplitude is not determined when it occurs, but only after the peak amplitude is determined, the peak amplitude occurring later in time.

It is understood by those skilled in the art that implementation of the various functions represented in FIG. 1 is accomplished from commercially available component parts. The pressure transducer employed converts pressure to an electrical analog current which is digitized by A/D converter 31. The remaining functional blocks are constructed primarily from commercially available microprocessors and other digital circuitry, excluding those items associated with the pneumatics and pneumatics controls. Power supplies are not shown, but are to be understood to be employed as required.

Figure 2:
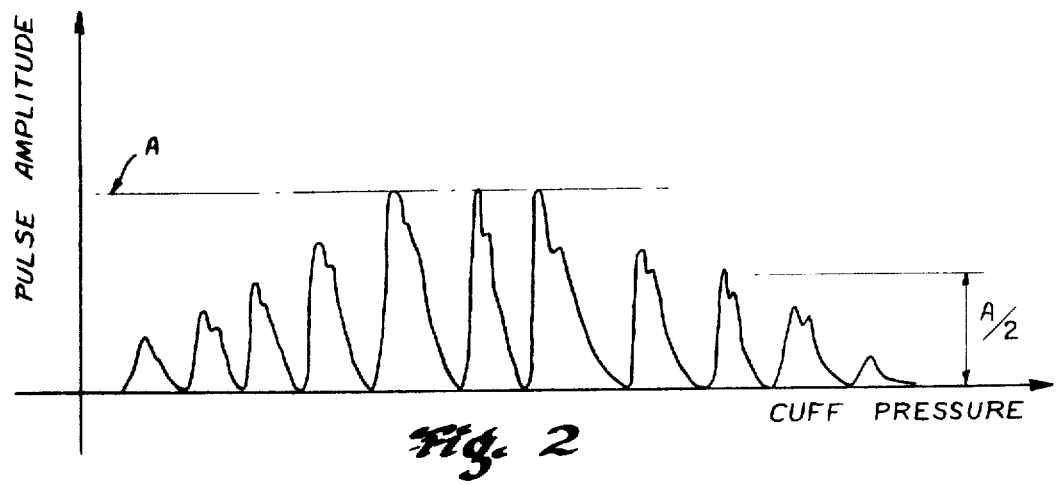
FIG. 2 illustrates a typical oscillometric envelope obtainable using the apparatus and method of the present invention.
Figure 3:
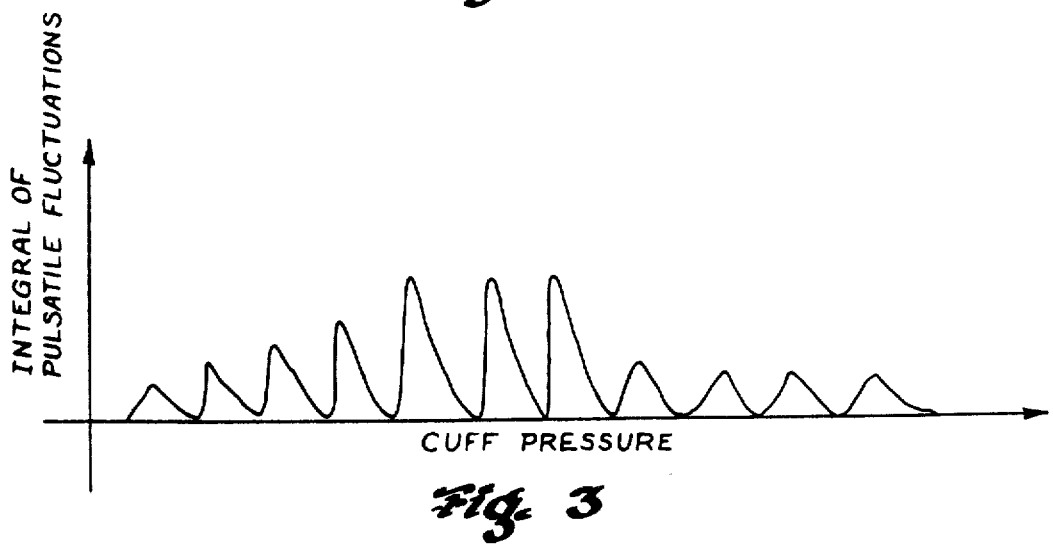
FIG. 3 illustrates an oscillometric envelope utilizing measuring means so that the pulses each represent the integral of the actual pulsatile pressure fluctuation within a blood vessel.

Referring now to FIGS. 2 and 3, one can observe the improved accuracy of systolic pressure measurements made with apparatus of the present invention. FIG. 2 is a plot of amplitude of the pulse height obtainable with apparatus and method of the present invention. The measuring means has a frequency response of preferably at least five times the subject's pulse rate. The maximum amplitude is labeled A and the half amplitude point (at cuff pressure higher than maximum amplitude cuff pressure) is labeled A/2. Corresponding applied cuff pressure is clearly discernable.

By contrast, FIG. 3 depicts an oscillometric envelope, as may be generated by a bouncing mercury column of a mercury manometer, or other integrator device. One observes that the threshold peak corresponding to half amplitude of FIG. 2 is difficult, at least, to define well.

THEORY

Figure 4:
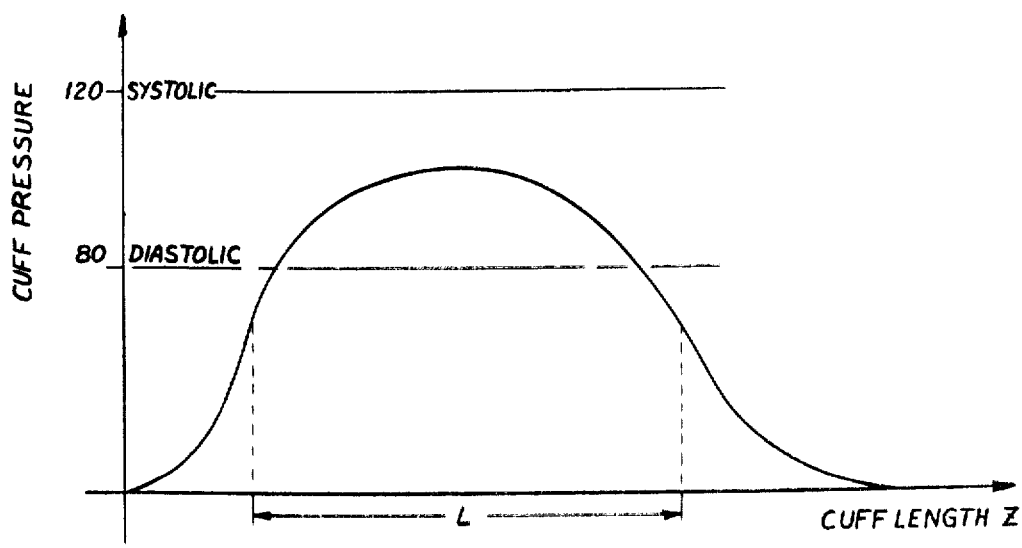
FIG. 4 illustrates the pressure applied to an artery as a function of arterial location within a cuff when the applied cuff pressure is between the systolic and diastolic pressure of the test subject.
Figure 5:
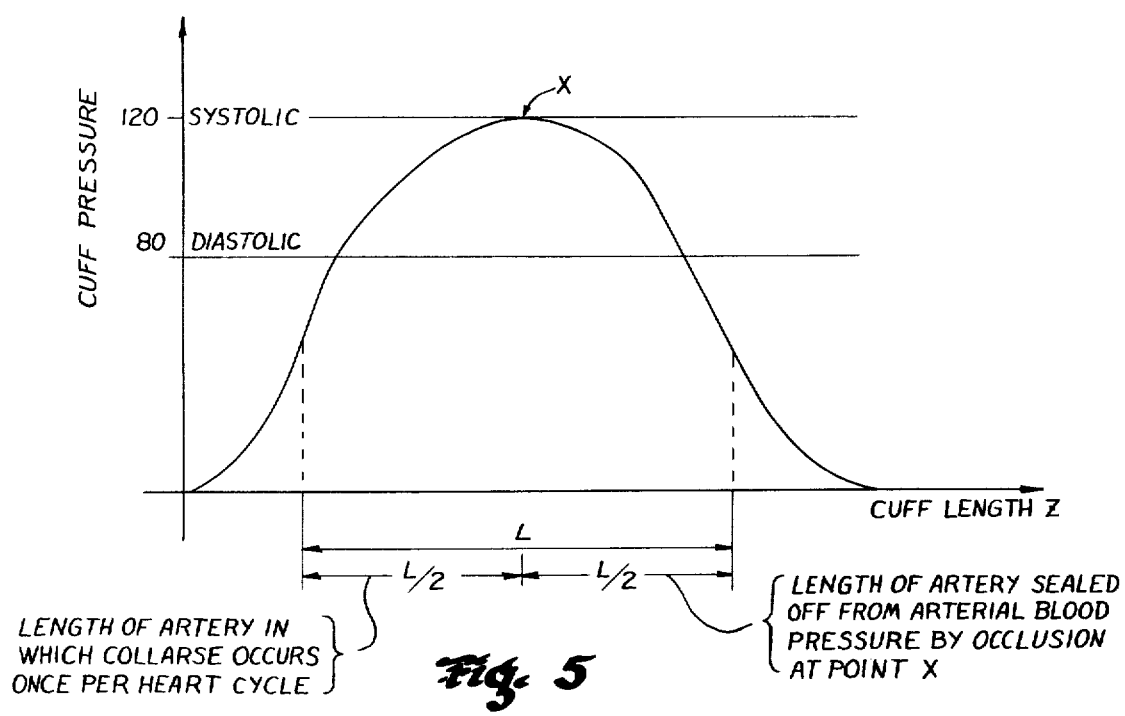
FIG. 5 illustrates the pressure applied to an artery as a function of arterial location within a cuff and the effect upon the artery when the pressure applied to the cuff is slightly greater than the systolic pressure of the test subject.
Figure 6:
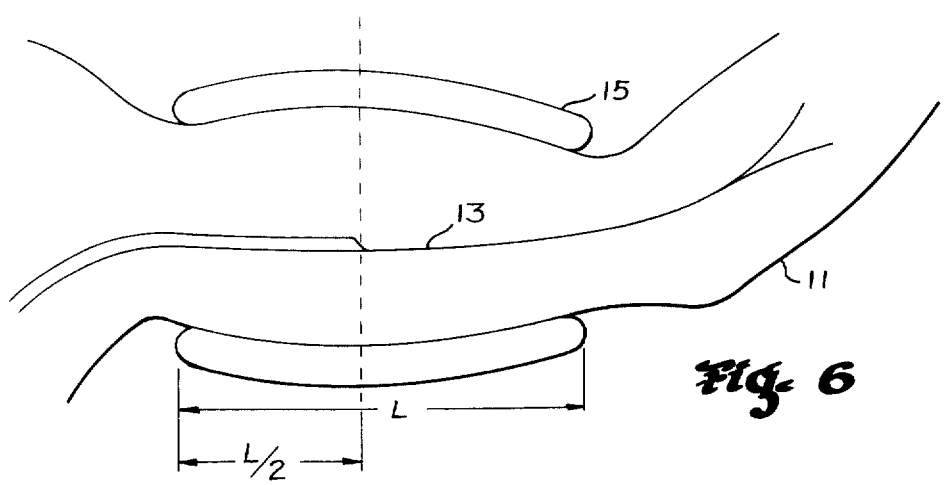
FIG. 6 illustrates an arm and the collapse of the brachial artery at point L/2 (half cuff length) when systolic pressure equals cuff pressure at L/2, as shown in FIG. 5.
Figure 7:
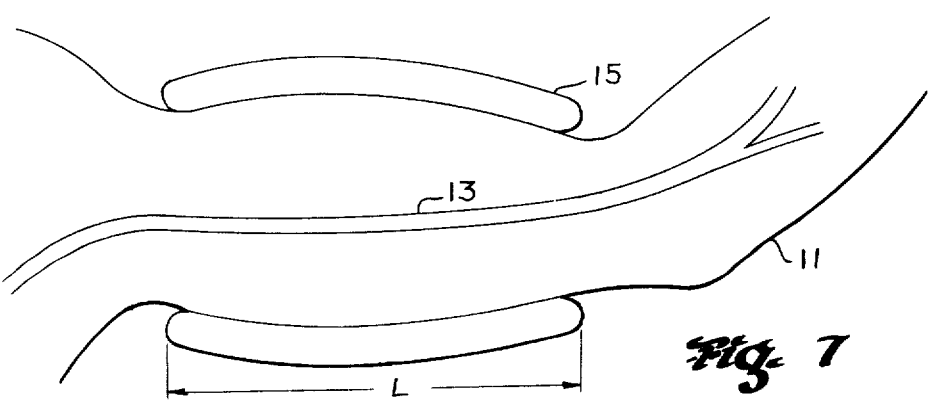
FIG. 7 illustrates an arm and the brachial artery without collapse, as would be obtained from cuff pressure less than systolic pressure, e.g., as shown in FIG. 4.

Referring to FIGS. 4 and 5 there is illustrated an explanation of our discovery as to why this relationship between maximum amplitude and one half maximum amplitude exists for determining systolic pressure. While it is believed that the following explanation of this phenomenon is correct, it is to be understood that the invention is not meant to be limited thereby. The figures illustrate arm 11 with artery 13 therein surrounded by cuff 15. The artery within the cuff is of length L. The pressure versus distance curve is aligned under the artery to illustrate pressure at the artery wall corresponding to an applied pressure between systolic and diastolic for FIG. 4 and slightly above systolic for FIG. 5. It will be noted that pressure at the artery wall is highest opposite the center of the cuff and drops off near edges thereof. This results because some of the cuff pressure adjacent ends of the cuff leads to the arm thereat being squeezed out of the cuff.

When pressure in the cuff is between diastolic and systolic pressure of the test subject, there is no part of the artery which is completely closed during an entire pulse. The artery is, of course, closed during the period when the pulse pressure is below the cuff pressure (in FIG. 4 when the pulse pressure is between 80 torr and 100 torr) but it is also, of course, open when the blood pressure is between cuff pressure (100 torr) and systolic pressure (120 torr). In this situation the artery 13 changes volume along its entire length L as the pressure changes from below to above 100 torr and vice versa. On the other hand, in the situation shown in FIG. 5 wherein applied pressure is just very slightly greater than systolic pressure of the test subject, it will be noted that one-half of the artery, namely that part of the artery distal from the heart, will for all practical purposes be constantly closed, since pulsatile pressure within the artery will never rise high enough to open it. This effect on one-half of the artery occurs because of the previously mentioned fact that only at the center of the cuff is the full applied cuff pressure also applied to the artery. This means that only one-half of the length of the artery changes volume as the blood pressure surges from diastolic to systolic during a pulse beat since only the portion of the artery proximal to the heart is opened against the pressure exerted at the artery wall by the cuff. Accordingly, the amplitude of the pressure fluctuation, which is just that quantity illustrated in FIG. 3, is to a good approximation one-half of the maximum fluctuation thereof which would comprise a fluctuation of the entire length L of the artery.

The invention may be embodied in yet other specific forms without departing from the spirit or essential characteristics thereof. For example, the applied cuff pressure may variably increase or decrease in any fashion including linear, nonlinear, and stepped (discontinuous) fashion. The apparatus for processing the transducer-generated electrical analog signal can be constructed from analog circuitry, digital circuitry, or both; specifically, discrete electronic components, discrete digital chips, microprocessor technology and structure, or a digital computer can be employed. The pressure cuff may be of the ordinary single cuff variety, but could also be a double cuff, or guarded cuff, etc. The cuff need not be an arm cuff, but could function on other limbs, fingers, etc.

Thus, the present embodiments are to be considered in all respects as illustrative and not restrictive, the scope of the invention being indicated by the appended claims rather than by the foregoing description, and all changes which come within the meaning and range of equivalency of the claims are therefore intended to be embraced therein.

That which is claimed is:

1. An apparatus for determining systolic pressure, comprising:

a pressure cuff attachable to a living test subject adjacent a blood vessel;

means for changing pressure in the cuff and thereby applying pressure to the subject;

means communicating with said cuff for measuring a quantity proportional to a time-dependent fluctuating component representative of the pulsatile pressure within the blood vessel, said means having a frequency response of at least about five times the pulse rate of the subject whereby said quantity is proportional to the amplitude of said pulsatile pressure;

means for determining the maximum value attained by said quantity as the applied pressure is changed;

means for storing a representation of said maximum value;

means for determining when said quantity is substantially equal to about one-half of said maximum value for an applied pressure greater than the pressure applied when said maximum value results; and means for reading out applied pressure corresponding to said quantity being substantially equal to about one-half of said maximum value, said read-out pressure corresponding to the systolic pressure of said subject.

2. An apparatus as in claim 1, wherein said quantity-measuring means comprises a pressure-transducer having a frequency response of at least about 10 Hertz.

3. An apparatus as in claim 2, wherein said pressure-changing means comprises a pump which applies an increasing pressure to said cuff between lower and upper pressure limits in a repetitive manner.

4. An apparatus as in claim 3, including means for stopping said pump and means for bleeding said cuff as said read-out of systolic pressure occurs.

5. An apparatus as in claim 4, wherein said means for determining said maximum value compreses a comparator wherein each successive representation of the value of said quantity is compared with a tentative previous representation of a maximum value thereof stored in said storing means, the lesser of the compared representations of the values of said quantity is discarded and the greater of the compared representations is stored in said storing means.

6. An apparatus as in claim 5, wherein said means for determining when said quantity is substantially equal to about one-half of said maximum value comprises a comparator wherein each successive representation of the value of said quantity is compared with one-half of the tentative representation of the maximum value of said quantity stored in said storing means, said stopping means and said bleeding means being activated when a value of said quantity is less than or equal to about one-half of said maximum value.

7. An apparatus as in claim 6, including a memory unit which temporarily stores a value of the applied pressure corresponding to each successive representation of the value of said quantity and also temporarily stores at least a value of the applied pressure corresponding to the previous to each successive representation of the value of said quantity.

8. An apparatus as in claim 7, including means for interpolating between stored values of representations of said quantity and between temporarily-stored values of the respective corresponding applied pressure to calculate an interpolated value of the applied pressure corresponding to when said quantity is substantially equal to about one-half of said maximum value.

9. A process for determining systolic pressure, comprising:

changing the pressure in a pressure cuff attached to a living test subject adjacent a blood vessel so as to apply different pressure to the subject;

measuring at said cuff with a measuring device having a frequency response of at least about five times the pulse rate of the subject at said cuff, a quantity proportional to a time-dependent fluctuating component representative of the pulsatile pressure within the blood vessel, said quantity being proportional to the amplitude of said pulsatile pressure;

determining the maximum value attained by said quantity as the applied pressure is changed;

storing a representation of said maximum value;

determining when said quantity is substantially equal to about one-half of said maximum value for an applied pressure greater than the pressure applied when said maximum value results; and reading out the applied pressure corresponding to said quantity being substantially equal to about one-half of said maximum value, said read-out pressure corresponding to the systolic pressure of said subject.

10. A process as in claim 9, wherein said quantity is measured utilizing a pressure transducer having a frequency response of at least about 10 Hertz.

11. A process as in claim 10, wherein said pressure is sequentially increased.

12. A process as in claim 11, including stopping said pump and bleeding said cuff as said read-out of systolic pressure occurs.

13. A process as in claim 12, including the step of interpolating between stored values of representations of said quantity and between temporarily-stored values of the respective corresponding applied pressure to calculate an interpolated value of the applied pressure corresponding to when said quantity is substantially equal to about one-half of said maximum value.

14. An automatic blood pressure monitoring system for measuring and monitoring systolic blood pressure of a person comprising:

transducer means in pressure-communication with said person for converting said person's blood pressure to a varying electrical analog signal;

pump means for applying a controllably variable pressure to said transducer means;

said transducer means including cuff means for applying said controllably variable pressure to a blood vessel of said subject;

converter means for receiving said electrical analog signal and converting said electrical analog signal to a digital signal;

digital processing means adapted to receive said digital signal for determining (1) maximum blood pressure of said person and a first value of said controllably variable pressure corresponding thereto, (2) one-half said maximum blood pressure when occurring at a second value of said controllably variable pressure higher than said first value, and (3) the magnitude of said second value; and means for providing read-out of said second value as systolic blood pressure.

15. A method for automatically measuring and monitoring systolic blood pressure of a person including the steps of:

A. converting said person's blood pressure to a varying electrical analog signal;

B. applying a controllably variable pressure to said person in a manner which affects said electrical analog signal;

C. converting said affected electrical analog signal to a digital signal;

D. digitally processing said signal to provide (1) maximum blood pressure of said person and a first value of said controllably variable pressure corresponding thereto; (2) one-half said maximum blood pressure when occurring at a second value of said controllably variable pressure higher than said first value; and (3) the magnitude of said second value; and E. providing read-out of said second value.

* * * * *